United States Patent
van der Louw et al.

(10) Patent No.: US 6,756,366 B1
(45) Date of Patent: Jun. 29, 2004

(54) ORALLY ACTIVE ANDROGENS

(75) Inventors: Jaap van der Louw, Oss (NL); Dirk Leysen, Lommel (BE); Roberta Burma Bursi, Hertogenbosch (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/937,274
(22) PCT Filed: Mar. 31, 2000
(86) PCT No.: PCT/EP00/02851
§ 371 (c)(1), (2), (4) Date: Sep. 24, 2001
(87) PCT Pub. No.: WO00/59920
PCT Pub. Date: Oct. 12, 2000

(30) Foreign Application Priority Data

Apr. 6, 1999 (EP) .............................. 99201070

(51) Int. Cl.$^7$ ........................ A61K 31/56; C07J 41/00; A24F 27/00
(52) U.S. Cl. ....................... 514/178; 206/112; 206/116; 206/126; 514/179; 514/182; 552/525; 552/539; 552/576; 552/621; 552/632; 552/639; 552/641
(58) Field of Search ................................ 552/625, 623; 514/182, 179, 178

(56) References Cited

U.S. PATENT DOCUMENTS 5,342,834 A    8/1994  Bardin et al. ................ 514/178
6,313,108 B1 * 11/2001 Loozen et al. .............. 514/178

FOREIGN PATENT DOCUMENTS

GB         1298974     * 12/1972

OTHER PUBLICATIONS

AN CA62:1704c, CAOLD; AN CA61:4426h, CAOLD (abstract of BE 623844).*
Solo, Alan J. et al.: "7.Alpha.–Alkyltestosterone Derivatives: Synthesis and Activity as Androgens and as Aromoatase Inhibitors", Steroids., vol. 40, No. 6, Dec. 1982, pp. 603–614.

* cited by examiner

Primary Examiner—Sabiha N. Qazi
(74) Attorney, Agent, or Firm—Mark W. Milstead; William M. Blackstone

(57) ABSTRACT

Orally Active androgens are derivative of 7α-methyl-19-nortestosterone. The compounds satisfy formula (I) wherein $R_1$ is O, (H,H), (H,OR), NOR, with R being hydrogen, $(C_{1-6})$alkyl, or $(C_{1-6})$acyl; $R_2$ is selected from the group consisting of $(C_{2-3})$alkyl, isopropyl, $(C_{2-3})$1-alkenyl, isopropenyl, 1,2-proandienyl, or $(C_{2-3})$1-alynyl, each optionally substituted by halogen; or $R_2$ is cyclopropyl, or cyclopropenyl, each optionally substituted by $(C_{1-2})$alkyl, or halogen; $R_3$ is hydrogen, $(C_{1-2})$alkyl, or ethenyl; $R_4$ is $(C_{1-2})$alkyl; $R_5$ is hydrogen, or $(C_{1-15})$acyl; and the dotted lines indicate optional bonds.

13 Claims, No Drawings

ORALLY ACTIVE ANDROGENS

The invention is in the field of androgenic hormones, more specifically derivatives of 19-nortestosterone.

Testosterone derivatives are known. As a medicine testosterone itself, the natural male hormone, has many known drawbacks as far as methods of administration are concerned. Thus, inter alia, it has a short-lasting activity and is not very potent. The more potent dihydrotestosterone (5α-reduced form of testosterone) is considered a health-risk, notably for the prostate.

A more potent androgen is 7α-methyl-19-nortestosterone (MENT) disclosed in FR 4,521 M and U.S. Pat. No. 5,342, 834. An important drawback of MENT, however, is its unfavourable kinetics which limits its use as an orally active androgen.

In the field of pharmaceutical preparations in general it is a common desire for a medicinal agent to be orally active. Oral dosage forms, e.g. solid dosage forms such as tablets and capsules, are among the most widely accepted forms of administration. In the field of androgens, a particular desire exists for the oral administration in connection with a utility such as male contraception. Since in the area of female contraception the word "pill" has almost become a synonym for reliable birth-control, it is evident that also in the case of male contraception oral activity is desired, so as to enable providing a male "pill."

Several, mostly very old publications can be mentioned which form the background-art relating to groups of steroid compounds which include 19-nortestosterone derivatives. None of these references teaches orally active androgens.

Thus, in FR 1,432,561, published in 1966, 19-nortestosterones like MENT having an alkyl substituent at C-7 are employed as a starting material for hormonal agents having a double bond between carbon atoms 5 and 6. Alkyl groups other than methyl are not disclosed.

BE 861 224 concerns all possible esters of a wide variety of 17-hydroxysteroids. The disclosure, which dates from 1976, specifically teaches that certain esters are desired for prolonged activity of the steroids. Among the large group of steroids disclosed are oestrogens, anti-oestrogens, androgens and anabolics. A great many possible substituents at various positions is given, among which are methyl and ethyl at C-7.

Chemical Abstracts 110: 95601y (1989) refers to the acetate of 7-allyl-19-nortestosterone as an intermediate in the synthesis of 7-allyloestradiol.

EP 159 739 teaches immunomodulating agents of the oestrane series, including particularly $\Delta^4$- and $\Delta^{5(10)}$-oestrene derivatives having an alkyl substituent in position 6 or 7. Said alkyl substituent typically is methyl.

DE 20 43 404 concerns 7β-steroids which have antihormonal activities. The alkyl substituent mostly is methyl, but ethyl and propyl are disclosed as well. In the synthesis of 7β-ethyl-19-nortestosterone, which is a compound according to the teaching of DE 20 43 404, the 7α-isomer is formed as well. It is not taught to use this isomer for anything, and the teaching of this document does not distinguish the ethyl or propyl substituents from the methyl moiety.

In a more recent patent application, EP 869 132, 7α-propyl-19-nortestosterone acetate is disclosed as an intermediate in the synthesis of certain estrogenic steroids. The disclosure does not bear any relevance to androgens, nor to any use of the above compound other than as a chemical intermediate.

The background art further includes A. J. Solo et al., in Steroids, 40 (6), 603–614 (1982) which relates to the androgenic and anabolic activities of certain 7α-alkyl testosterones.

It is an object of the invention to provide orally active androgens. A further object of the invention is to provide androgens which in general have a desirable high potency. According to the invention, these and other objectives are achieved by compounds satisfying the general formula I given below.

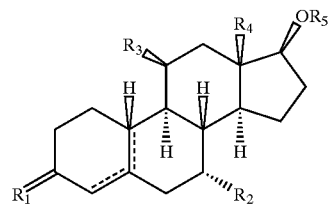

Formula I wherein

R₁ is O, (H,H), (H,OR), NOR, with R being hydrogen, $(C_{1-6})$alkyl, or $(C_{1-6})$acyl;

R₂ is $(C_{2-3})$alkyl, isopropyl, $(C_{2-3})$1-alkenyl, isopropenyl, 1,2-propadienyl, or $(C_{2-3})$1-alkynyl, each optionally substituted by halogen; or R₂ is cyclopropyl, or cyclopropenyl, each optionally substituted by $(C_{1-2})$ alkyl or halogen;

R₃ is hydrogen, $(C_{1-2})$alkyl, or ethenyl;

R₄ is $(C_{1-2})$alkyl;

R₅ is hydrogen, or $(C_{1-15})$acyl;

and the dotted lines indicate optional bonds;

with the proviso that the compound is not (7α,17β)-7-ethyl-17-hydroxyestr-4-en-3-one (7α-ethyl-19-nortestosterone) or a carboxylic ester thereof, and is not (7α,17β)-17-(acetyloxy)-7-propylestr-4-en-3-one (7α-propyl-19-nortestosterone acetate).

The proviso is made in the recognition that the disclaimed compounds have been incidentally disclosed as intermediates in chemical synthesis, in DE 20 43 404 and EP 869 132, respectively. It is stressed that these compounds, as are the other compounds of the invention, are novel for use as a medicine in general, as an androgen, and more particularly as an orally active androgen. Hence, also the compounds disclaimed per se, form part of the present invention and the description hereinafter applies to these compounds as well.

The term $(C_{1-6})$alkyl as used in the definition of formula I means a branched or unbranched alkyl group having 1–6 carbon atoms, like methyl, ethyl, propyl, isopropyl, butyl, isobutyl, tertiary butyl, pentyl, and hexyl. Likewise, the term $(C_{1-2})$alkyl means an alkyl group having 1–2 carbon atoms and the term $(C_{2-3})$alkyl an alkyl group having 2–3 carbon atoms.

The term $(C_{2-3})$alkenyl means an alkenyl group having 2–3 carbon atoms. Preferred is ethenyl.

The term $(C_{2-3})$alkynyl means an alkynyl group having 2–3 carbon atoms. Preferred is ethynyl.

The term $(C_{1-6})$acyl means an acyl group derived from a carboxylic acid having from 1–6 carbon atoms, like formyl, acetyl, propanoyl, butyryl, 2-methylpropanoyl, pentanoyl, pivaloyl, and hexanoyl. Likewise, the term $(C_{1-15})$acyl means an acyl group derived from a carboxylic acid having from 1–15 carbon atoms. Also included within the definition of $(C_{1-15})$acyl are

[$(C_{3-6})$cycloalkyl]carbonyl,

[$(C_{5-6})$cycloalkenyl]carbonyl, benzoyl,

[[$(C_{1-12})$alkyl]$(C_{3-6})$cycloalkyl]carbonyl,

[[($C_{2-12}$)alkenyl]($C_{3-6}$)cycloalkyl]carbonyl],
[[($C_{2-12}$)alkynyl]($C_{3-6}$)cycloalkyl]carbonyl],
[[($C_{1-10}$)alkyl]($C_{5-6}$)cycloalkenyl]carbonyl],
[[($C_{2-10}$)alkenyl]($C_{5-6}$)cycloalkenyl]carbonyl],
[[($C_{2-10}$)alkynyl]($C_{5-6}$)cycloalkenyl]carbonyl],
($C_{1-9}$)alkylbenzoyl,
($C_{2-9}$)alkenylbenzoyl,
($C_{2-9}$)alkynylbenzoyl.

Also included within the definition of ($C_{1-6}$)acyl or ($C_{1-15}$)acyl are acyl groups derived from dicarboxylic acids, like hemi-maloyl, hemi-succinoyl, hemi-glutaroyl, and so on. Preferred is hemi-succinoyl.

The term halogen means fluorine, chlorine, bromine, or iodine. When halogen is a substituent at an alkyl group, Cl and F are preferred, F being most preferred.

It is understood that the 7α-substituted nandrolone derivatives of the invention have the natural configurations 5α, 8β, 9α, 10β, 13β, 14α, 17β.

The 7α-substituted nandrolone derivatives of this invention have the natural configurations 5α, 8β, 9α, 10β, 13β, 14α and 17β, and possess also one or more additional chiral carbon atoms. The compounds may therefore be obtained as a pure diastereomer, or as a mixture of diastereomers. Methods for obtaining the pure diastereomers are well known in the art, e.g. crystallization or chromatography.

Unlike the known compound (MENT), which possesses a 7α-methyl substituent, the compounds of formula I, which can be referred to as 7α-substituted nandrolones, surprisingly have sufficient androgenic potency upon oral administration. None of the above, mostly very old references teaches orally active androgens, let alone that they provide the person skilled in the art with a clue to distinguish any other substituent at C-7 from the widely used methyl moiety.

Preferred compounds have $R_2$ selected from the group consisting of ethyl, ethenyl, ethynyl, propyl, 1-propenyl, 1-propynyl, 1,2-propadienyl, and cyclopropyl.

Even more preferred are compounds in which $R_1$ is oxo, $R_3$ is hydrogen, $R_4$ is methyl or ethyl, and the dotted lines indicate a $\Delta^4$ double bond.

Most preferred are those compounds in which $R_2$ is $C_2$, with the highest preference being ethyl or ethenyl.

The invention also pertains to the compounds described hereinbefore as a medicine. The 7α-substituted nandrolones of the present invention being potent androgens, they can be used in, int.al., male contraception and male or female hormone replacement therapy. Thus the invention also pertains to a method of treatment of androgen insufficiency, by administering to a human male or female an effective amount of any of the above compounds. The invention also is in the use of any of the above compounds for the preparation of a medicine for treating androgen insufficiency. In the context of the invention, the term "androgen insufficiency" is to be understood to pertain to all kinds of diseases, disorders, and symptoms in which a male or a female suffers from too low a testosterone level, such as in hypogonadal men. In particular, the androgen insufficiency to be treated by the compound of the invention is the reduction of the testosterone level which a human male incurs as a result of age (the compound of the invention is then used for male hormone replacement therapy), or when he is subject to male contraception. In the context of male contraception, the compound of the invention especially serves to neutralise the effect of regimens of male hormone contraception in which a sterilitant such as a progestagen or LHRH (luteinizing hormone releasing hormone) is administered regularly, e.g. daily, or it is used as the sole male contraceptive substance.

The androgens can be administered principally via any suitable route available to the skilled person. As indicated above, oral administration is preferred, most preferably in the form of a solid dosage unit such as a tablet or a capsule. The invention also relates to pharmaceutical formulations comprising a compound as described hereinbefore and a pharmaceutically acceptable carrier. Thus the carrier may be in a solid form or liquid form, and the formulation may be an oral dosage unit such as a tablet or an oral solution, e.g. in a capsule. Methods and compositions for making such dosage units are well-known to those skilled in the art. For example, conventional techniques for making tablets and pills, containing active ingredients, are described in the standard reference, Gennaro et al, Remington's Pharmaceutical Sciences, (18th ed., Mack Publishing Company, 1990, see especially Part 8: Pharmaceutical Preparations and Their Manufacture). The compound can also be administered via an implant, a patch, or any other suitable device for the sustained release of an androgen composition.

The dose of and regimen of administration of the compounds of the invention, or a pharmaceutical composition thereof, to be administered will obviously depend on the therapeutic effect to be achieved and will vary with the route of administration, and the age and condition of the individual subject to whom the medicament is to be administered, and/or or the particular contraceptive or HRT regimen in which it is used. Typical dosage amounts are 0.001–5 mg per kg body weight.

The compounds of the invention may be produced by various methods known in the art of organic chemistry in general, and especially in the art of the chemistry of steroids (see, for example: Fried, J. et al, *Organic Reactions in Steroid Chemistry*, Volumes I and II, Van Nostrand Reinhold Company, New York, 1972).

Essential is the introduction of a saturated or unsaturated 7α-substituent, optionally substituted by halogen, onto the steroid nucleus.

For 7α-substitution, several methodologies are known in the art, among others:

1)—Conjugate addition (1,6-addition) of organocopper reagents to suitably substituted (17β)-17-hydroxyestra-4,6-dien-3-one derivatives, in which the 17-hydroxy group is protected as an ester, e.g. an acetate ester or a benzoate ester, or as an alkoxyalkyl ether, e.g. an ethoxyethyl ether or a tetrahydropyranyl ether, or as a silyl ether, e.g. a trimethylsilyl ether or a t-butyldimethylsilyl ether [for conjugate additions of organocopper reagents, see Lipshutz, B. H. et al in Org. Reactions 41, p. 135, Wiley, New York, 1992].

2)—Transition metal-mediated ($TiCl_4$, $AlCl_3$, $ZrCl_4$, etc.) reaction of an organosilicon compound with a (17β)-17-hydroxyestra-4,6-dien-3-one derivative as described above [again formal 1,6-addition; see e.g. Nickisch, K. et al, Tetrahedron Lett. 29, 1533 (1988)].

3)—Base-catalyzed conjugate addition (1,6-addition) of a dialkyl malonate or alkyl cyanoacetate to a (17β)-17-hydroxyestra-4,6-dien-3-one derivative as described above [see e.g. Cruz, R. et al, Austr. J. Chem. 35, 451 (1982)].

4)—Lewis acid-catalyzed reaction of an estra-1,3,5(10),7-tetraene derivative with an aldehyde (Prins reaction), resulting in an estra-1,3,5(10),8-tetraene-7-alkanol derivative [see: Kuenzer, H. et al, Tetrahedron Lett. 32, 743 (1991)].

5)—Alkylation at C-7 of an estra-1,3,5(10)-trien-6-one derivative [see: e.g. Tedesco, R. et al, Tetrahedron Lett. 38, 7997 (1997)].

6)—Conjugate addition (1,4-addition) of a suitable nucleophilic reagent (e.g. an organocopper reagent) to a 6-[alkyl(or aryl)sulfonyl]estra-1,3,5(10),6-tetraen derivative [Schering AG, DE 42 18 743 A 1].

Using these methodologies, the compounds of the invention can further be prepared using standard methods known in the art.

The invention will be further explained hereinafter with reference to the following Examples.

EXAMPLE 1

(7α,17β)-7-Ethyl-17-hydroxyestr-4-en-3-one i)—A mixture of lithium (0.647 g) and dry diethyl ether (26 ml) was cooled to −30° C. Bromoethane (3.45 ml) was added dropwise while maintaining the temperature below −25° C. After 30 min. stirring at −30° C. the solution of ethyllithium was added dropwise to a suspension of copper (I) iodide (4.0 g) in dry tetrahydrofuran (40 ml), cooled to −40° C. The resulting cuprate solution was stirred at −30° C. for 30 min. and a solution of (17β)-17-[[(1,1-dimethylethyl)dimethylsilyl]oxy]estra-4,6-dien-3-one [Nickisch, K. et al, Tetrahedron Lett. 29, 1533 (1988); 2.5 g] in dry tetrahydrofuran (20 ml) was added dropwise. Stirring was continued at −30° C. for 30 min., chlorotrimethylsilane (2.58 ml) was added and stirring was continued for another 30 min. The reaction mixture was poured into a mixture of a saturated aqueous solution of ammonium chloride and concentrated ammonia (9:1). The product was extracted into ethyl acetate; the combined organic phases were washed with a saturated aqueous solution of sodium hydrogencarbonate, water and brine, dried over magnesium sulfate and concentrated under reduced pressure, to give (7α,17β)-17-[[(1,1-dimethylethyl)dimethylsilyl]oxy]-7-ethyl-3-[(trimethylsilyl)oxy]estra-3,5-diene (2.81 g). The product was used in the following step without further purification.

ii)—A solution of the diene obtained in the previous step (2.81 g) in acetone (60 ml) was treated with hydrochloric acid (6 M, 6.0 ml). After 1 h stirring at room temperature, the reaction mixture was neutralized with a saturated aqueous solution of sodium hydrogencarbonate. The product was extracted into ethyl acetate; the combined organic phases were washed with water and brine, dried over magnesium sulfate and concentrated under reduced pressure. Column chromatography and crystallization afforded (7α,17β)-7-ethyl-17-hydroxyestr-4-en-3-one (0.556 g), m.p. 142.5–143.5° C.

EXAMPLE 2

(7α,17β)-7-Ethyl-17-hydroxyestr-5(10)-en-3-one i)—A solution of (7α,17β)-7-ethyl-17-hydroxyestr-4-en-3-one (Example 1, 2.0 g) in dry pyridine (15 ml) was treated with acetic anhydride (1.86 ml) and the reaction mixture was stirred at room temperature for 6.5 h; additional acetic anhydride (1.86 ml) was added after 3 h. The mixture was cooled to 0° C.; water was added and stirring was continued for 30 min. The product was extracted into ethyl acetate; the combined organic phases were washed with water and brine, dried over magnesium sulfate and concentrated under reduced pressure, to give (7α,17β)-17-(acetyloxy)-7-ethylestr-4-en-3-one (2.15 g). The product was used in the next step without further purification.

ii)—A mixture of the product obtained in the previous step (2.15 g), trimethyl orthoformate (2.5 ml) and copper(II) bromide (2.06 g), in methanol (55 ml) was heated under reflux for 1.5 h. After cooling, the reaction mixture was filtered. The residue was washed with ethyl acetate and the filtrate was concentrated. Then it was washed with a saturated aqueous solution of sodium hydrogencarbonate, water and brine, dried over magnesium sulfate and concentrated under reduced pressure. Column chromatography afforded (7α,17β)-7-ethyl-3-methoxyestra-1,3,5(10)-trien-17-ol (1.43 g).

iii)—The product obtained in the previous step (1.25 g) in dry tetrahydrofuran (25 ml) was added to a refluxing solution of lithium (0.84 g) in liquid ammonia (150 ml). After 2 h stirring, tert-butanol (6 ml) was added and stirring was continued for 30 min. Ethanol was added and the ammonia was allowed to evaporate. The mixture was poured into water and the product was extracted into ethyl acetate. The combined organic phases were washed with water and brine, dried over sodium sulfate and concentrated under reduced pressure, to give (7α,17β)-7-ethyl-3-methoxyestra-2,5(10)-dien-17-ol (1.25 g). The product was used in the following step without further purification.

iv)—A solution of the product obtained in the previous step (1.25 g) in a mixture of methanol (12 ml) and tetrahydrofuran (8.5 ml) was treated with a solution of oxalic acid (0.42 g) in water (7 ml). After 1.5 h stirring at room temperature, the reaction mixture was poured into water and the product was extracted into ethyl acetate. The combined organic phases were washed with a saturated aqueous solution of sodium hydrogencarbonate, water and brine, dried over sodium sulfate and concentrated under reduced pressure. Column chromatography afforded (7α,17β)-7-ethyl-17-hydroxyestr-5(10)-en-3one (0.52 g), $^1$H NMR δ 3.70 (m, 1H), 2.74 (bs, 2H), 0.90 (t, 3H, J=7.2 Hz), 0.77 (s, 3H).

EXAMPLE 3

(7α,17β)-17-Hydroxy-7-propylestr-4-en-3-one i)—Following procedures analogous to those described under Example 1, (17β)-17-(acetyloxy)estra-4,6-dien-3-one [Syntex, DE 1143199 (1963); 75.00 g], was converted to (17β)-17-(acetyloxy)-7-propylestr-4-en-3-one (87.88 g).

ii)—A solution of potassium hydroxide (0.16 g) in water (1.5 ml) was added to a solution of the product obtained in the previous step (0.50 g) in a mixture of tetrahydrofuran (5 ml) and methanol (5 ml). The reaction mixture was stirred at room temperature for 2.5 h and then poured into water. The product was extracted into ethyl acetate; the combined organic phases were washed with water and brine, dried over magnesium sulfate and concentrated under reduced pressure. Column chromatography afforded (7α,17β)-17-hydroxy-7-propylestr-4-en-3-one (0.15 g), $[α]_D^{20}$=+38.4° (c=0.505, dioxane).

EXAMPLE 4

(7α,17β)-7-Ethenyl-17-hydroxyestr-4-en-3-one i)—Vinylmagnesium chloride in tetrahydrofuran (2 M, 9.55 ml) was added dropwise to a mixture of (17β)-17-(acetyloxy)estra-4,6-dien-3-one (Example 3, step i; 3.0 g), copper(I) bromide-dimethyl sulfide complex (0.191 g), lithium bromide (0.083 g), and lithium thiophenoxide (0.96 ml of a 1 M solution in tetrahydrofuran), in dry tetrahydrofuran (10 ml), cooled to −15° C. After 25 min. stirring a saturated aqueous solution of ammonium chloride was added and the product extracted into ethyl acetate. The combined organic phases were concentrated under reduced pressure whereafter the residue was dissolved in acetone (100 ml) and treated with hydrochloric acid (4 M, 10 ml). After 30 min. stirring at room temperature, a saturated aqueous solution of sodium hydrogencarbonate was added. The product was extracted into ethyl acetate; the combined organic phases were washed with brine, dried over sodium sulfate and concentrated under reduced pressure, to give (7α,17β)-17-(acetyloxy)-7-ethenylestr-4-en-3-one (3.76 g). The product was used in the following step without further purification.

ii)—Following a procedure analogous to that described under ii of Example 3, the product obtained in the previous step (3.76 g) was converted to (7α,17β)-7-ethenyl-17-hydroxyestr-4-en-3-one (1.68 g), m.p. 130.5–133.5° C.

EXAMPLE 5

[7α(E),17β]-7-(2-Chloroethenyl)-17-hydroxyestr-4-en-3-one (a) and [7α(Z),17β]-7-(2-chloroethenyl)-17-hydroxyestr-4-en-3-one (b)

i)—A solution of (7α,17β)-17-[[(1,1-dimethylethyl)dimethylsilyl]oxy]-3-methoxyestra-1,3,5(10),8-tetraene-7-methanol [Kuenzer, H. et al, Tetrahedron Lett. 32, 743 (1991); 7.3 g] in dry tetrahydrofuran (100 ml) was added to liquid ammonia (400 ml), cooled at −40° C. Lithium granulate (3.58 g) was added and the reaction mixture was stirred at reflux temperature for 1 h. Ethanol (22.1 ml) was added carefully and the mixture was stirred for 30 min. Solid ammonium chloride was added and the ammonia was allowed to evaporate. Water was added and the product was extracted into ethyl acetate. The combined organic phases were washed with water and brine, dried over magnesium sulfate and concentrated under reduced pressure, to give (7α,17β)-17-[[(1,1-dimethylethyl)dimethylsilyl]oxy]-3-methoxyestra-2,5(10)-diene-7-methanol (7.22 g). The product was used in the following step without further purification.

ii)—Following a procedure analogous to that described under i of Example 2, the product obtained in the previous step (7.22 g) was converted to (7α,17β)-7-[(acetyloxy)methyl]-17-[[(1,1-dimethylethyl)dimethylsilyl]oxy]-3-methoxyestra-2,5(10)-diene (7.80 g).

iii)—Following a procedure analogous to that described under ii of Example 1, the diene described above (15.9 g) was converted to (7α,17β)-7-[(acetyloxy)methyl]-17-hydroxyestr-4-en-3-one (4.10 g).

iv)—Boron trifluoride diethyl etherate (1.34 ml) was added to a mixture of the ketone obtained in the previous step (3.52 g), 1,2-ethanedithiol (2.82 ml) and dry methanol (32 ml), cooled to 0° C. After 2 h stirring the reaction mixture was filtered; the residue was washed with water and dissolved in dichloromethane. The dichloromethane solution was washed with water and brine, dried over magnesium sulfate and concentrated under reduced pressure, to give (7α,17β)-7-[(acetyloxy)methyl]-17-hydroxyestr-4-en-3-one cyclic 1,2-ethanediyl dithioacetal (4.21 g). The product was used in the following step without further purification.

v)—A solution of the product obtained in the previous step (4.21 g) and imidazole (4.75 g) in dry dimethylformamide (80 ml) was cooled to 0° C. and treated with t-butyldimethylsilyl chloride (6.01 g). After 2 h stirring the reaction mixture was poured into water. The product was extracted into ethyl acetate; the combined organic phases were washed with water and brine, dried over magnesium sulfate and concentrated under reduced pressure. Column chromatography afforded (7α,17β)-7-[(acetyloxy)methyl]-17-[[(1,1-dimethylethyl)dimethylsilyl]oxy]estr-4-en-3-one cyclic 1,2-ethanediyl dithioacetal (6.0 g).

vi)—A solution of the product obtained in the previous step (5.9 g) in dry tetrahydrofuran (70 ml) was added dropwise to an ice-cooled suspension of lithium aluminium hydride (1.25 g) in tetrahydrofuran (140 ml). After stirring of the mixture for 45 min., the reaction was quenched by addition of a saturated aqueous solution of sodium sulfate. Ethyl acetate was added, and the mixture was filtered over dicalite. The filtrate was concentrated under reduced pressure to give (7α,17β)-17-[[(1,1-dimethylethyl)dimethylsilyl]oxy]-7-(hydroxymethyl)estr-4-en-3-one cyclic 1,2-ethanediyl dithioacetal (4.66 g). The product was used in the following step without further purification.

vii)—Tetrapropylammonium perruthenate (0.200 g) was added to a solution of the product obtained in the previous step (4.66 g) and 4-methylmorpholine N-oxide (3.31 g) in acetone (70 ml). After 4 h stirring at room temperature additional portions of 4-methylmorpholine N-oxide (0.65 g) and tetrapropylammonium perruthenate (0.010 g) were added and stirring was continued for another 2 h. The reaction mixture was filtered over dicalite and silica. The filtrate was concentrated under reduced pressure, to give (7α,17β)-17-[[(1,1-dimethylethyl)dimethylsilyl]oxy]-7-formylestr-4-en-3-one cyclic 3-(1,2-ethanediyl dithioacetal) (4.50 g) which was used in the following step without further purification.

viii)—A suspension of (chloromethyl)triphenylphosphonium chloride (3.52 g) in dry tetrahydrofuran (100 ml) was cooled to 0° C. Sodium t-butoxide (0.917 g) was added and the mixture was stirred for 30 min. A solution of the aldehyde obtained in the previous step (1.0 g) in dry tetrahydrofuran (15 ml) was added and the reaction mixture was stirred at room temperature for 2 h. Then it was poured into water and the product was extracted into ethyl acetate. The combined organic phases were washed with a saturated aqueous solution of sodium hydrogencarbonate, water and brine, dried over magnesium sulfate and concentrated under reduced pressure. Column chromatography afforded a mixture of [7α(E),17β]-7-(2-chloroethenyl)-17-[[(1,1-dimethylethyl)dimethylsilyl]oxy]estr-4-en-3-one cyclic 1,2-ethanediyl dithioacetal and [7α(Z),17β]-7-(2-chloroethenyl)-17-[[(1,1-dimethylethyl)dimethylsilyl]oxy]estr-4-en-3-one cyclic 1,2-ethanediyl dithioacetal (0.60 g, 3:1).

ix)—A solution of periodic acid (0.011 g) in a mixture of methanol and water (1:1, 0.60 ml) was added to a solution of the product obtained in the previous step (0.10 g) in dichloromethane (1 ml). After 1 h stirring at room temperature the reaction mixture was poured into a saturated aqueous solution of sodium hydrogencarbonate. The product was extracted into dichloromethane; the combined organic phases were washed with a saturated aqueous solution of sodium thiosulfate, water and brine, dried over magnesium sulfate and concentrated under reduced pressure, to give a mixture of [7α(E),17β]-7-(2-chloroethenyl)-17-[[(1,1-dimethylethyl)dimethylsilyl]oxy]estr-4-en-3-one and [7α(Z),17]-7-(2-chloroethenyl)-17-[[(1,1-dimethylethyl)dimethylsilyl]oxy]estr-4-en-3-one (0.080 g). The product was used in the following step without further purification.

x)—Following a procedure analogous to that described under ii of Example 1, the product obtained in the previous step (0.070 g) was desilylated, to produce a mixture of [7α(E),17β]-7-(2-chloroethenyl)-17-hydroxyestr-4-en-3-one and [7α(Z),17β]-7-(2-chloroethenyl)-17-hydroxyestr-4-en-3-one (0.025 g). A part of this mixture (0.01 g) was separated by preparative HPLC to afford [7α(E),17β]-7-(2-chloroethenyl)-17-hydroxyestr-4-en-3-one (7.0 mg), $^1$H NMR δ 6.01 (d, 1H, J=13.0 Hz), 5.86 (m, 1H), 5.83 (dd, 1H, J=13.0 and 9.1 Hz), 3.67 (t, 1H, J=8.3 Hz), 0.81 (s, 3H); and [7α(Z),17β]-7-(2-chloroethenyl)-17-hydroxyestr-4-en-3-one (2.5 mg), $^1$H NMR δ 6.09 (d, 1H, J=7.1 Hz), 5.80 (m, 1H), 5.69 (dd, 1H, J=10.6 and 7.1 Hz), 3.64 (t, 1H, J=8.3 Hz), 3.16 (m, 1H), 0.81 (s, 3H).

EXAMPLE 6

[7α(E),17β]-17-Hydroxy-7-(1-propenyl)estr-4-en-3-one (a, Method A) and [7α(Z),17β]-17-hydroxy-7-(1-propenyl)estr-4-en-3-one (b)

i)—Potassium t-butoxide (0.346 g) was added to a suspension of ethyltriphenylphosphonium bromide (1.21 g) in dry tetrahydrofuran (10 ml) and the mixture was stirred for 1 h at 50° C. A solution of (7α,17β)-17-[[(1,1-dimethylethyl)dimethylsilyl]oxy]-7-formylestr-4-en-3-one cyclic 3-(1,2-ethanediyl dithioacetal) (Example 5, step vii; 0.40 g) in dry tetrahydrofuran (2 ml) was added and stirring was continued for another 1 h. Then it was poured into water and the product was extracted into ethyl acetate. The combined organic phases were washed with water and brine, dried over magnesium sulfate and concentrated under reduced pressure. Column chromatography afforded a mixture of [7α(E),17β]-17-[[(1,1-dimethylethyl)dimethylsilyl]oxy]-7-(1-propenyl)estr-4-en-3-one cyclic 1,2-ethanediyl dithioacetal and [7α(Z),17β]-17-[[(1,1-dimethylethyl)dimethylsilyl]oxy]-7-(1-propenyl)estr-4-en-3-one cyclic 1,2-ethanediyl dithioacetal (0.317 g, 1:3).

ii)—Following a procedure analogous to that described under ii of Example 1, the product obtained in the previous step (0.317 g) was desilylated, to produce a mixture of [7α(E),17β]-17-hydroxy-7-(1-propenyl)estr-4-en-3-one cyclic 1,2-ethanediyl dithioacetal and [7α(Z),17β)]-17-hydroxy-7-(1-propenyl)estr-4-en-3-one cyclic 1,2-ethanediyl dithioacetal (0.32 g).

iii)—Following a procedure analogous to that described under ix of Example 5, the product obtained in the previous step (0.32 g) was converted to the 3-oxo compound, to produce a mixture of [7α(E),17β]-17-hydroxy-7-(1-propenyl)estr-4-en-3-one and [7α(Z),17β]-17-hydroxy-7-(1-propenyl)estr-4-en-3-one (0.083 g). A part of this mixture (0.025 g) was separated by preparative HPLC to afford [7α(E),17β]-17-hydroxy-7-(1-propenylestr-4-en-3-one (3.5 mg), $^1$H NMR δ 5.83 (m, 1H), 5.49 (dq, 1H, J=15.4 and 6.7 Hz), 5.31 (ddq, 1H, J=15.4, 8.3 and 1.4 Hz), 3.65 (t, 1H, J=7.9 Hz), 1.65 (dd, 3H, J=6.7 and 1.4 Hz), 0.80 (s, 3H); and [7α(Z),17β]-17-hydroxy-7-(1-propenyl)estr-4-en-3-one (14.0 mg), $^1$H NMR δ 5.78 (m, 1H), 5.51 (dq, 1H, J=11.0 and 7.1 Hz), 5.31 (tq, 1H, J=11.0 and 1.4 Hz), 3.64 (t, 1H, J=8.3 Hz), 2.85 (m, 1H), 1.63 (dd, 3H, J=7.1 and 1.4 Hz), 0.81 (s, 3H).

EXAMPLE 7

[7α(E),17β]-17-Hydroxy-7-(1-propenyl)estr-4-en-3-one (Method B)

Following a procedure analogous to that described under i of Example 4, using trans-1-propenylmagnesium bromide [prepared by dropwise addition of a solution of trans-1-bromo-1-propene (6.67 ml) in tetrahydrofuran (75 ml) to a suspension of magnesium (1.98 g), activated with 1,2-dibromoethane, in the same solvent (15 ml), while maintaining the temperature below 30° C.], (17β)-17-[[(1,1-dimethylethyl)dimethylsilyl]oxy]estra-4,6-dien-3-one (Example 1; 10.0 g) was converted to [7α(E),17β]-17-hydroxy-7-(1-propenyl)estr-4-en-3-one (0.72 g), $[α]_D^{20}$=−28.3° (c=0.92, dioxane).

EXAMPLE 8

(7α,17β)-7-Ethynyl-17-hydroxyestr-4-en-3-one i)—Following a procedure analogous to that described under iv of Example 2, (7α,17β)-7-[(acetyloxy)methyl]-17-[[(1,1-dimethylethyl)dimethylsilyl]oxy]-3-methoxyestra-2,5(10)-diene (Example 5, step ii; 4.88 g) was converted to (7α,17β)-7-[(acetyloxy)methyl]-17-[[(1,1-dimethylethyl)dimethylsilyl]oxy]estr-5(10)-en-3-one (1.91 g).

ii)—p-Toluenesulfonic acid (0.020 g) was added to a solution of the ketone obtained in the previous step (1.91 g) in methanol (40 ml) and trimethyl orthoformate (2.3 ml). After 10 min. stirring at room temperature the reaction mixture was poured into a saturated aqueous solution of sodium hydrogencarbonate and the product was extracted into ethyl acetate. The combined organic phases were washed with water and brine, dried over magnesium sulfate and concentrated under reduced pressure, to give (7α,17β)-7-[(acetyloxy)methyl]-17-[[(1,1-dimethylethyl)dimethylsilyl]oxy]estr-5(10)-en-3-one dimethyl acetal (1.77 g). The product was used in the following step without further purification.

iii)—Following a procedure analogous to that described under vi of Example 5, the product obtained in the previous step (1.77 g) was converted to (7α,17β)-17-[[(1,1-dimethylethyl)dimethylsilyl]oxy]-7-(hydroxymethyl)estr-5(10)-en-3-one dimethyl acetal (1.58 g).

iv)—Following a procedure analogous to that described under vii of Example 5, the product obtained in the previous step (1.58 g) was converted to (7α,17β-17-[[(1,1-dimethylethyl)dimethylsilyl]oxy]-7-formylestr-5(10)-en-3-one 3-(dimethyl acetal) (2.0 g).

v)—Following a procedure analogous to that described under viii of Example 5, the product obtained in the previous step (2.0 g) was converted to a mixture of [7α(E),17β]-7-(2-chloroethenyl)-17-[[(1,1-dimethylethyl)dimethylsilyl]oxy]estr-5(10)-en-3-one dimethyl acetal and [7α(Z),17β]-7-(2-chloroethenyl)-17-[[(1,1-dimethylethyl)dimethylsilyl]oxy]estr-5(10)-en-3-one dimethyl acetal (0.90 g, 3:1).

vi)—A solution of the product obtained in the previous step (0.90 g) in dry tetrahydrofuran (30 ml) was cooled to −15° C. and then treated with n-BuLi in hexanes (1.6 M, 1.5 ml). After 10 min. stirring at −15° C. and 20 min. at room temperature another portion of n-BuLi in hexanes (1.6 M, 1.0 ml) was added and after 15 min. a third portion of n-BuLi in hexanes (1.6 M, 0.5 ml) was added. Stirring was continued for 1.25 h. The reaction mixture was poured into a saturated aqueous solution of sodium hydrogencarbonate and the product was extracted into ethyl acetate. The combined organic phases were washed with water and brine, dried over magnesium sulfate and concentrated under reduced pressure. Column chromatography afforded (7α,17β)-17-[[(1,1-dimethylethyl)dimethylsilyl]oxy]-7-ethynylestr-5(10)-en-3-one dimethyl acetal (0.40 g).

vii)—Following a procedure analogous to that described under ii of Example 1, the product obtained in the previous step (0.24 g) was converted to (7α,17β)-7-ethynyl-17-hydroxyestr-4-en-3-one (0.117 g), $[α]_D^{20}$=+38.0° (c=0.395, dioxane).

EXAMPLE 9

(7α,17β)-17-Hydroxy-7-(1-propynyl)estr-4-en-3-one i)—A solution of (7α,17β)-17-[[(1,1-dimethylethyl)dimethysilyl]oxy]-7-ethynylestr-5(10)-en-3-one dimethyl acetal (Example 8, step vi; 0.12 g) in dry tetrahydrofuran (2.5 ml) was cooled to −20° C. and then treated with n-BuLi in hexanes (1.6 M, 0.41 ml). After 30 min. stirring at −20° C., iodomethane (0.066 ml) was added and stirring was continued for 15 min. Another portion of iodomethane (0.066 ml) was added and stirring was continued for 1 h at 0° C. The reaction mixture was poured into water and the product was extracted into ethyl acetate. The combined organic phases Were washed with water and brine, dried over magnesium sulfate and concentrated under reduced pressure. Column chromatography afforded (7α,17β-17-[[(1,1-dimethylethyl)dimethylsilyl]oxy]-7-(1-propynyl)estr-5(10)-en-3-one dimethyl acetal (0.051 g). The product was used in the following step without further purification.

ii)—Following a procedure analogous to that described under ii of Example 1, the product obtained in the previous step (0.051 g) was converted to (7α,17β)-17-hydroxy-7-(1-propynyl)estr-4-en-3-one (0.030 g), $[\alpha]_D^{20}$=+29.4° (c=0.35, dioxane).

EXAMPLE 10

(7α,17β)-7-Cyclopropyl-17-hydroxyestr-4-en-3-one i)—Chlorotrimethylsilane (19 ml) was added in 5 min. to a suspension of (17α)-17-hydroxy-19-norpregna-4,6-dien-20-yn-3-one [Syntex, GB 935116 (1958); 18.0 g] in a mixture of dichloromethane (300 ml) and pyridine (25 ml), cooled to 0° C. After 2 h stirring at 0° C. the reaction mixture was poured into a saturated aqueous solution of sodium hydrogencarbonate. The product was extracted into dichloromethane; the combined organic phases were washed with water and brine, dried over sodium sulfate and concentrated under reduced pressure, to afford (17α)-17-[(trimethylsilyl)oxy]-19-norpregna-4,6-dien-20-yn-3-one (22.3 g). The product was used in the following step without further purification.

ii)—A mixture of the product described above (60.7 g), diethyl malonate (126 ml), sodium methoxide (9 g), and dry ethanol (165 ml) was stirred at room temperature for 24 h. Part of the ethanol was removed (80 ml) and stirring was continued for another 24 h. Again part of the ethanol was removed (25 ml) and the reaction mixture was stirred for an additional 24 h. The mixture was poured into a saturated aqueous solution of ammonium chloride and the product was extracted into ethyl acetate. The combined organic phases were concentrated under reduced pressure and dissolved in acetone (400 ml). Hydrochloric acid (6 M, 20 ml) was added and the reaction mixture was stirred at room temperature for 2 h. A saturated aqueous solution of sodium hydrogencarbonate was added and the acetone was removed under reduced pressure. The product was extracted into ethyl acetate; the combined organic phases were washed with brine, dried over sodium sulfate and concentrated. Column chromatography afforded diethyl 2-[(7α,17α)-17-hydroxy-3-oxo-19-norpregn-4-en-20-yn-7-yl]propanedioate (33.8 g).

iii)—A mixture of the product obtained in the previous step (14.4 g), copper(II) bromide (14.3 g), and lithium bromide (2.84 g) in acetonitrile (288 ml) was stirred at room temperature for 1 h. The reaction mixture was poured into a mixture of a saturated aqueous solution of ammonium chloride and a saturated aqueous solution of ammonia (9:1) and the product was extracted into ethyl acetate. The combined organic phases were washed with a saturated aqueous solution of sodium hydrogencarbonate and brine, dried over sodium sulfate and concentrated under reduced pressure. Column chromatography afforded diethyl 2-[(7α,17α)-3,17-dihydroxy-19-norpregna-1,3,5(10)-trien-20-yn-7-yl]propanedioate (13.6 g).

iv)—Following a procedure analogous to that described under v of Example 5, the product obtained in the previous step (12.5 g) was converted to diethyl 2-[(7α,17α)-3-[[(1,1-dimethylethyl)dimethylsilyl]oxy]-17-hydroxy-19-norpregna-1,3,5(10)-trien-20-yn-7-yl]propanedioate (15.3 g).

v)—A mixture of the product obtained in the previous step (7.50 g) and copper(II) carbonate on dicalite (16.5 g) in toluene (112 ml) was heated at reflux temperature for 2.5 h under removal of water by use of a Dean-Stark trap. The reaction mixture was filtered and the filtrate was concentrated under reduced pressure, to give diethyl 2-[(7α)-3-[[(1,1-dimethylethyl)dimethylsilyl]oxy]-17-oxoestra-1,3,5(10)trien-7-yl]propanedioate (7.07 g). The product was used in the following step without further purification.

vi)—p-Toluenesulfonic acid (0.36 g) was added to a solution of the ketone obtained in the previous step (7.07 g) in ethylene glycol (12 ml) and triethyl orthoformate (21 ml). After 1.5 h stirring at room temperature water (200 ml) was added and stirring was continued for 1 h. The product was extracted into ethyl acetate; the combined organic phases were washed with a saturated aqueous solution of sodium hydrogencarbonate and brine, dried over sodium sulfate and concentrated under reduced pressure, to give diethyl 2-[(7α)-3-[[(1,1-dimethylethyl)dimethylsilyl]oxy]-17,17-[1,2-ethanediylbis(oxy)]estra-1,3,5(10)-trien-7-yl]propanedioate (8.48 g). The product was used in the following step without further purification.

vii)—Following a procedure analogous to that described under vi of Example 5, the product obtained in the previous step (8.48 g) was converted to (7α)-7-(1,3-dihydroxyprop-2-yl)-3-[[(1,1-dimethylethyl)dimethylsilyl]oxy]estra-1,3,5(10)-trien-17-one cyclic 1,2-ethanediyl acetal (3.0 g).

viii)—Methanesulfonyl chloride (4.60 ml) was added to a solution of the diol obtained in the previous step (3.0 g) in dry pyridine (116 ml), cooled to 0° C. After 35 min. stirring the reaction mixture was poured into water and the product was extracted into ethyl acetate. The combined organic phases were washed with brine, dried over sodium sulfate, and concentrated under reduced pressure, to give (7α)-7-[1,3-bis[(methylsulfonyl)oxy]prop-2-yl]-3-[[(1,1-dimethylethyl)dimethylsilyl]oxy]estra-1,3,5(10)-trien-17-one cyclic 1,2-ethanediyl acetal (4.08 g). The product was used in the following step without further purification.

ix)—A mixture of the product obtained in the previous step (2.0 g), sodium iodide (3.45 g), zinc powder (3.14 g), water (4.1 ml) and dimethoxyethane (41 ml) was heated under reflux for 3.5 h. After cooling, the reaction mixture was filtered. The filtrate washed with a saturated aqueous solution of sodium thiosulfate and brine, dried over sodium sulfate and concentrated under reduced pressure, to afford (7α)-7-cyclopropyl-3-[[(1,1-dimethylethyl)dimethylsilyl]oxy]estra-1,3,5(10)-trien-17-one cyclic 1,2-ethanediyl acetal (1.47 g). The product was used in the following step without further purification.

x)—Following a procedure analogous to that described under ii of Example 1, the product obtained in the previous step (1.47 g) was converted to (7α)-7-cyclopropyl-3-hydroxyestra-1,3,5(10)-trien-17-one (0.63 g).

xi)—Sodium borohydride (0.45 g) was added to a solution of the compound obtained in the previous step (0.63 g) in a mixture of tetrahydrofuran (8.3 ml), ethanol (8.3 ml), water (1.4 ml) and pyridine (0.05 ml). The reaction mixture was stirred at room temperature for 1.25 h and then poured into water. The product was extracted into ethyl acetate. The combined organic phases were washed with a saturated aqueous solution of sodium hydrogencarbonate and brine, dried over sodium sulfate and concentrated, to give (7α,17β)-7-cyclopropylestra-1,3,5(10)-triene-3,17-diol (0.710 g). The product was used in the following step without further purification.

xii)—A mixture of the product obtained in the previous step (0.29 g), dry potassium carbonate (0.77 g), iodomethane (0.35 ml) and dry dimethylformamide (0.87 ml) was stirred at room temperature overnight. The mixture was poured into a saturated aqueous solution of ammonium chloride and the product was extracted into ethyl acetate. The combined organic phases were washed with a saturated aqueous solution of sodium hydrogencarbonate and brine, dried over sodium sulfate and concentrated under reduced pressure. Column chromatography afforded (7α,17β)-7-cyclopropyl-3-methoxyestra-1,3,5(10)-trien-17-ol (0.096 g).

xiii)—Following a procedure analogous to that described under i of Example 5, using tert-butanol instead of ethanol, the product described above (0.167 g) was converted to (7α,17β)-7-cyclopropyl-3-methoxyestra-2,5(10)-dien-17-ol (0.24 g).

xiv)—Following a procedure analogous to that described under ii of Example 1, the product obtained in the previous step (0.24 g) was converted to (7α,17β)-7-cyclopropyl-17-hydroxyestr-4-en-3-one (0.081 g), m.p. 154–158° C.

EXAMPLE 11

(7α,11β,17β)-7-Ethyl-17-hydroxy-11-methylestr-4-en-3-one i)—Pyridinium p-toluenesulfonate (1.65 g) was added to a solution of (11β)-11-methylestr-4-ene-3,17-dione [van den Broek, A. J. et al, Steroids 30, 481 (1977); 16.86 g] in a mixture of ethanol (110 ml), dioxane (220 ml) and triethyl orthoformate (35.0 ml). After 4 h stirring at room temperature pyridine was added and the reaction mixture was poured into a saturated aqueous solution of sodium hydrogencarbonate. The product was extracted into ethyl acetate; the combined organic phases were washed with water and brine, dried over magnesium sulfate and concentrated under reduced pressure, to give (11β)-3-ethoxy-11-methylestra-3,5-dien-17-one (21.84 g). The product was used in the following step without further purification.

ii)—A solution of the product obtained in the previous step (24.0 g) in tetrahydrofuran (90 ml), containing pyridine (1 ml), was added to a suspension of tetrachloro-1,4-benzoquinone (20.7 g) in a mixture of ethanol (220 ml) and water (25 ml). The reaction mixture was stirred at room temperature for 5 h and then treated with a solution of sodium hydrogensulfite (11.1 g) in water (160 ml). After 30 min. stirring, a saturated aqueous solution of sodium sulfite was added and the product was extracted into ethyl acetate. The combined organic phases were washed with a saturated aqueous solution of sodium sulfite, water and brine, dried over magnesium sulfate and concentrated under reduced pressure. Column chromatography afforded (11β)-11-methylestra-4,6-diene-3,17-dione (10.1 g).

iii)—A solution of the product obtained in the previous step (9.3 g) in a mixture of methanol (93 ml) and dichloromethane (46 ml), cooled to −20° C., was treated with a solution of sodium borohydride (0.494 g) in methanol (166 ml), containing sodium hydroxide (1.0 g). The reaction mixture was stirred at −10° C. for 5 h and then quenched with acetone (62 ml). The mixture was poured into water and the product was extracted into ethyl acetate. The combined organic phases were washed with water and brine, dried over magnesium sulfate and concentrated under reduced pressure, to give (11β,17β)-17-hydroxy-11-methylestra-4,6-dien-3-one (7.70 g). The product was used in the following step without further purification.

iv)—Following a procedure analogous to that described under v of Example 5, the product obtained in the previous step (7.20 g) was converted to (11β,17β)-17-[[(1,1-dimethylethyl)dimethylsilyl]oxy]-11-methylestra-4,6-dien-3-one (5.70 g).

v)—Following a procedure analogous to that described under i of Example 4, using ethyl magnesium bromide, the product obtained in the previous step (1.0 g) was converted to (7α,11β,17β)-7-ethyl-17-hydroxy-11-methylestr-4-en-3-one (0.12 g), $^1$H NMR δ 5.86 (m, 1H), 3.62 (m, 1H), 1.07 (d, 3H, J=7.9 Hz), 0.88 (s, 3H), 0.86 (t, 3H, J=7.5 Hz).

EXAMPLE 12

(7α,11β,17β)-7-Ethenyl-17-hydroxy-11-methylestr-4-en-3-one

Following a procedure analogous to that described under i of Example 4, (11β,17β)-17-[[(1,1-dimethylethyl)dimethylsilyl]oxy]-11-methylestra-4,6-dien-3-one (Example 11, step iv; 1.30 g) was converted to (7α,11β,17β)-7-ethenyl-17-hydroxy-11-methylestr-4-en-3-one (0.070 g), $^1$H NMR δ 5.84 (m, 1H), 5.73 (m, 1H), 5.14–5.05 (m, 2H), 3.59 (m, 1H), 1.08 (d, 3H, J=7.9 Hz), 0.88 (s, 3H).

EXAMPLE 13

(7α,17β)-7,13-Diethyl-17-hydroxygon-4-en-3-one i)—Following a procedure analogous to that described under i of Example 11, 13-ethylgon-4-ene-3,17-dione [Hoffmann-La Roche and Co.; AG, DE 1806410 (1967); 100.0 g] was converted to 3-ethoxy-13-ethylgona-3,5-dien-17-one (146.3 g). ii)—Following a procedure analogous to that described under vi of Example 5, the product obtained in the previous step (146.3 g) was converted to (17β)-3-ethoxy-13-ethylgona-3,5-dien-17-ol (115.0 g).

iii)—Following a procedure analogous to that described under ii of Example 11, the product obtained in the previous step (115.0 g) was converted to (17β)-13-ethyl-17-hydroxygona-4,6-dien-3-one (56.3 g).

iv)—Following a procedure analogous to that described under v of Example 5, the product obtained in the previous step (56.3 g) was converted to (17β)-17-[[(1,1-dimethylethyl)dimethylsilyl]oxy]-13-ethylgona-4,6-dien-3-one (65.6 g).

v)—Following a procedure analogous to that described under i of Example 4, using ethyl magnesium bromide, the product obtained in the previous step (25.0 g) was converted to (7α,17β)-7,13-diethyl-17-hydroxygon-4-en-3-one (3.18 g), m.p. 161.5–162.5° C.

EXAMPLE 14

(7α,17β)-7-Ethenyl-13-ethyl-17-hydroxygon-4-en-3-one

Following a procedure analogous to that described under i of Example 4, (17β)-17-[[(1,1-dimethylethyl)dimethylsilyl]oxy]-13-ethylgona-4,6-dien-3-one (Example 13, step iv; 25.0 g) was converted to (7α,17β)-7-ethenyl-13-ethyl-7-hydroxygon-4-en-37-one (1.18 g), m.p. 155.1–156.3° C.

EXAMPLE 15

(7α,17β)-7-Ethylestr-4-en-17-ol i)—Following a procedure analogous to that described under iv of Example 5, (7α,17β)-7-ethyl-17-hydroxyestr-4-en-3-one (Example 1; 1.50 g) was converted to (7α,17β)-7-ethyl-17-hydroxyestren-3-one cyclic 1,2-ethanediyl dithioacetal (1.32 g).

ii)—A solution of the product obtained in the previous step (1.32 g) in dry tetrahydrofuran (5 ml) was added to a solution of sodium (0.72 g) in liquid ammonia (70 ml), cooled to −40° C. After 1 h stirring, dry ethanol was added and the ammonia was allowed to evaporate. Water was added and the product was extracted into ethyl acetate. The combined organic phases were washed with aqueous sodium hydroxide (1 M), water and brine, dried over sodium sulfate and concentrated under reduced pressure. Column chromatography afforded (7α,17β)-7-ethylestr-4-en-17-ol (0.62 g), m.p. 155–157° C.

EXAMPLE 16

(7α,17β)-7-Ethenylestr-4-en-17-ol

The title compound was prepared from (7α,17β)-7-ethenyl-17-hydroxyestr-4-en-3-one (Example 4) in a manner analogous to that described under Example 15. M.p. 117–121° C.

EXAMPLE 17

(3β,7α,17β)-7-Ethylestr-4-ene-3,17-diol

Following a procedure analogous to that described under vi of Example 5, the title compound was prepared from (7α,17β)-7-ethyl-17-hydroxyestr-4-en-3-one (Example 1). M.p. 93–95° C.

EXAMPLE 18

(3α,7α,17β)-7-Ethylestr-4-ene-3,17-diol i)—Following a procedure analogous to that described under v of Example 5, (7α,17β)-7-ethyl-17-hydroxyestr-4-en-3-one (Example 1; 2.0 g) was converted to (7α,17β)-17-[[(1,1-dimethylethyl)dimethylsilyl]oxy]-7-ethylestr-4-en-3-one (2.58 g).

ii)—Following a procedure analogous to that described under vi of Example 5, the product obtained in the previous step (2.58 g) was converted to (3β,7α,17β)-17-[[(1,1-dimethylethyl)dimethylsilyl]oxy]-7-ethylestr-4-en-3-ol (2.30 g).

iii)—Diethyl azodicarboxylate (1.20 ml) was added dropwise to an ice-cooled solution of the product obtained in the previous step (2.04 g), triphenylphosphine (1.91 g) and p-nitrobenzoic acid (1.22 g) in dry toluene (60 ml). The reaction mixture was stirred for 1 h and then poured into a saturated aqueous solution of ammonium chloride. The product was extracted into ethyl acetate; the combined organic phases were washed with water and brine, dried over magnesium sulfate and concentrated under reduced pressure. Column chromatography afforded (3α,7α,17β)-17-[[(1,1-dimethylethyl)dimethylsilyl]oxy]-7-ethylestr-4-en-3-ol p-nitrobenzoate (3.20 g).

iv)—The product obtained in the previous step (1.92 g) was dissolved in a solution of tetrabutylammonium fluoride in tetrahydrofuran (1 M, 40 ml). The reaction mixture was stirred overnight and then poured into water. The product was extracted into ethyl acetate; the combined organic phases were washed with a saturated aqueous solution of sodium hydrogencarbonate, water and brine, dried over magnesium sulfate and concentrated under reduced pressure. Column chromatography afforded (3α,7α,17β)-7-ethylestrene-3,17-diol 3-p-nitrobenzoate (0.93 g).

v)—Following a procedure analogous to that described under ii of Example 4, the product obtained in the previous step (0.93 g) was converted to (3α,7α,17β)-7-ethylestr-4-ene-3,17-diol (0.25 g), m.p. 134.8–136.5° C.

EXAMPLE 19

(3α,7α,17β)-7-Ethylestr-5(10)-ene-3,17-diol (a) and (3β,7α,17β)-7-ethylestr-5(10)-ene-3,17-diol (b)

Sodium borohydride (0.013 g) was added to a solution of (7α,17β)-7-ethyl-17-hydroxyestr-5(10)en-3-one (Example 2; 0.25 g) in a mixture of tetrahydrofuran (4.2 ml) and methanol (4.2 ml). The reaction mixture was stirred at room temperature for 2 h and then quenched with acetone. The mixture was poured into water and the product was extracted into ethyl acetate. The combined organic phases were washed with water and brine, dried over magnesium sulfate and concentrated under reduced pressure. Column chromatography afforded (3α,7α,17β)-7-ethylestr-5(10)-ene-3,17-diol, m.p. 98–100° C., and (3β,7α,17β)-7-ethylestr-5(10)-ene-3,17-diol, m.p. 60–65° C.

EXAMPLE 20

(3E,7α,17β)-7-Ethenyl-3-(hydroxyimino)estr-4-en-17-ol (a) and (3Z,7α,17β)-7-ethenyl-3-(hydroxyimino)estr-4-en-17-ol (b)

To a solution of (7α,17β)-7-ethenyl-17-hydroxyestr-4-en-3-one (Example 4; 1.63 g) in pyridine (9.4 ml) was added hydroxylamine hydrochloride (4.15 g). The reaction mixture was stirred at 80° C. for 50 min. After cooling, the mixture was poured into water (118 ml). The product was extracted into ethyl acetate; the combined organic phases were washed with brine, dried over sodium sulfate and concentrated under reduced pressure. Column chromatography afforded (3E,7α,17β)-7-ethenyl-3-(hydroxyimino)estr-4-en-17-ol (0.60 g), $[\alpha]_D^{20}$=−4.8° (c=1.00, dioxane), and (3Z,7α,17β)-7-ethenyl-3-(hydroxyimino)estr-4-en-17-ol (0.65 g), m.p. 206–224° C.

EXAMPLE 21

The LH Suppression Assay

The in vivo potency of several androgens of the invention was determined in a mature male castrated rat model, in comparison with MENT.

In this model serum LH is high (50× fold higher than with intact rats, due to the absence of the negative feedback of testicular testosterone). These rats are po treated for 4 days daily with a given compound of the invention in a suspension fluid of arachisoil. Before dosing and 3 hours after the last oral dose blood is collected via tail vene and in the serum LH is determined. Potency of the androgens ($ED_{50}$) are expressed as the amount (mg/kg) of androgen which suppresses serum LH for 50% (±10%).

The rat LH Time-Resolved Immuno Fluorometric Assay (TR-IFMA) has been developed in house using home made reagents, a monoclonal catching antibody directed against the β-subunit of human chorion gonadotrophin (hCG, which cross react with rat β-subunit) and a biotin labelled detecting antibody (rabbit polyclonal antibody directed against the alfa-subunit of recombinant rat LH). Recombinant rat LH was prepared according to the methods described by Hakola et al (1997). In this two-site-IFMA, only intact rat LH is determined by a final incubation with streptavidin-europium. The detection in the IFMA is based on fluorescence of the lanthanide europium during a relative long exitation period. The concentration range of rat LH standard is 0.001–10 ng/ml, for optimal accuracy measurements of serum LH serum samples were diluted 8-times with assay buffer [Hakola, K., Boogaart, P. V., Mulders, J., de Leeuw, R., Schoonen, W., Heyst, J. V., Swolfs, A., Casteren, J. V., Huhtaniemi, I., and Kloosterboer, H. J., *Recombinant rat luteinizing hormone; production by Chinese hamster ovary cells, purification and functional characterization*, Molecular & Cellular Endocrinology 128, 47 (1997)].

Results

Table. $ED_{50}$ (po) of androgens of the invention required to suppress serum LH for 50% (±10%).

TABLE $ED_{50}$(po) of androgens of the invention required to suppress serum LH for 50% (±10%).

| Example | $ED_{50}$ (mg/kg) |
|---|---|
| 1 | 2.5 |
| 4 | 2.5 |
| 11 | 5 |
| 12 | 5 |
| MENT | 10 |

EXAMPLE 22

Determination of $t_{1/2}$ of Androgens of the Invention After Incubation with Human Hepatocytes The half-life of a compound as a result of contact with human hepatocytes holds as a reliable indication of metabolic stability. As it is well known that the absorption of this class of steroids is high, this assay provides an in vitro model for oral activity in humans. It will be understood that a shorter half-life indicates that a compound will be metabolized more rapidly or, vice versa, the longer the half-life, the better the compound may exert its effect upon the human body when administered orally.

Hepatocytes collected from healthy young (25–45 year) male organ donors were cryo preserved in liquid nitrogen and kept there until use. They were thawed at 37° C. in a waterbath, placed immediately on ice, washed twice in one volume of cold (4° C.) incubation medium [William's medium E (without phenol red) with Glutamax I®, gentamicin 50 μg/ml, insulin 1 μM, hydrocortisone hemisuccinate 10 μM, fetal calf serum 0% (v/v)], counted and the viability checked by Trypan blue exclusion. Cells were incubated as suspensions in 12-wells (non-coated) plates at a nominal density of 0.5×10⁶ cells/well in 1.5 ml medium at 37° C. with an air/$O_2$/$CO_2$ mixture (55/40/5). The plates were set on an orbital shaker at approximately 10 rpm.

The hepatocytes were incubated with 10 nM final concentration of the compound to be tested. The incubations were stopped after 0.5, 1 and 3 h by pipetting the whole incubation mixture into a glass tube and adding one volume of acetone on ice. The acetone was dried under a nitrogen flow at room temperature, the volume adjusted to 1.5 ml and the tubes were centrifuged at 4° C. at 10.000×g for 30 min. The de-proteinized supernatants were collected for LC-MS/MS analysis.

Results

Table $t_{1/2}$ of androgens of the invention after incubation with human hepatocytes.

TABLE $t_{1/2}$ of androgens of the invention after incubation with human hepatocytes.

| Example | $t_{1/2}$(min) |
|---|---|
| 1 | 48 |
| 6a | 30 |
| 10 | 30 |
| 13 | 48 |
| 14 | 20 |
| MENT | 20 |

What is claimed is:

1. A compound of the structural formula:

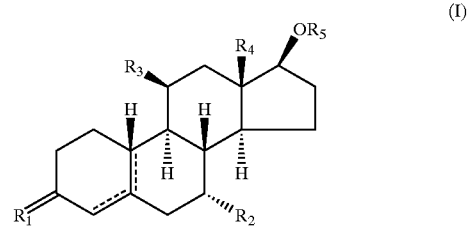

(I)

wherein $R_1$ is O, (H,H), (H,OR), NOR, with R being hydrogen, $(C_{1-6})$alkyl, or $(C_{1-6})$acyl;

$R_2$ is isopropyl, $(C_{2-3})$1-alkenyl, isopropenyl, 1,2-propadienyl, or $(C_{2-3})$1-alkynyl, each optionally substituted by halogen; or $R_2$ is cyclopropyl, or cyclopropenyl, each optionally substituted by $(C_{1-2})$ alkyl or halogen;

$R_3$ is hydrogen, $(C_{1-2})$alkyl, or ethenyl;

$R_4$ is $(C_{1-2})$alkyl;

$R_5$ is hydrogen, or $(C_{1-15})$acyl; and the dotted lines indicate optional bonds.

2. The compound according to claim 1, wherein $R_2$ is selected from the group consisting of ethenyl, ethynyl, 1-propenyl, 1-propynyl, 1,2-propadienyl, and cyclopropyl.

3. The compound according to claim 1, wherein $R_1$ is oxo, $R_3$ is hydrogen, and the dotted lines indicate a $\Delta^4$ double bond.

4. The compound according to claim 1, wherein $R^2$ is ethenyl.

5. The compound according to claim 1, selected from the group consisting of (7α,17β)-7-Ethenyl-13-ethyl-17-hydroxygon-4-en-3-one.

6. A pharmaceutical composition, comprising:

a pharmaceutically acceptable carrier and a steroid compound, as a medicinally active agent, satisfying formula I

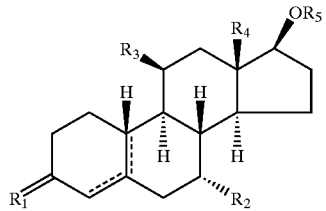

(I)

wherein

R₁ is O, (H,H), (H,OR), NOR, with R being hydrogen, (C₁₋₆)alkyl, or (C₁₋₆)acyl;

R₂ is isopropyl, (C₂₋₃)1-alkenyl, isopropenyl, 1,2-propadienyl, or (C₂₋₃)1-alkynyl, each optionally substituted by halogen; or R₂ is cyclopropyl, or cyclopropenyl, each optionally substituted by (C₁₋₂) alkyl or halogen;

R₃ is hydrogen, (C₁₋₂)alkyl, or ethenyl;

R₄ is (C₁₋₂)alkyl;

R₅ is hydrogen, or (C₁₋₁₅)acyl; and the dotted lines indicate optional bonds.

7. The pharmaceutical composition according to claim 6, wherein R² is selected from the group consisting of ethenyl, ethynyl, 1-propenyl, 1-propynyl, 1,2-propadienyl, and cyclopropyl.

8. The pharmaceutical composition according to claim 7, wherein the steroid compound is selected from the group consisting of (7α,17β)-7-ethenyl-13-ethyl-17-hydroxygon-4-en-3-one.

9. The pharmaceutical composition according to claim 6 suitable for oral administration.

10. A kit for male contraception comprising a progestagen and an androgen, wherein the androgen is a compound according to claim 1.

11. A method of treatment of androgen insufficiency, comprising:

administering to a patient in need thereof an effective amount of an androgen, wherein the androgen is a steroid compound satisfying formula I

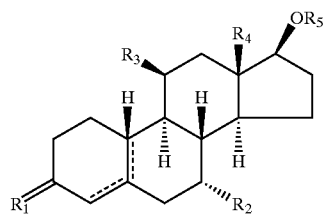

(I)

wherein

R₁ is O, (H,H), (H,OR), NOR, with R being hydrogen, (C₁₋₆)alkyl, or (C₁₋₆)acyl;

R₂ is isopropyl, (C₂₋₃)1-alkenyl, isopropenyl, 1,2-propadienyl, or (C₂₋₃)1-alkynyl, each optionally substituted by halogen; or R₂ is cyclopropyl, or cyclopropenyl, each optionally substituted by (C₁₋₂) alkyl or halogen;

R₃ is hydrogen, (C₁₋₂)alkyl, or ethenyl;

R₄ is (C₁₋₂)alkyl;

R₅ is hydrogen, or (C₁₋₁₅)acyl; and the dotted lines indicate optional bonds.

12. The method of treatment according to claim 11, wherein R₂ is selected from the group consisting of ethenyl, ethynyl, 1-propenyl, 1-propynyl, 1,2-propadienyl, and cyclopropyl.

13. The method of treatment according to claim 12, wherein the steroid compound is selected from the group consisting of (7α,17β)-7-ethenyl-13-ethyl-17-hydroxygon-4-en-3-one.

\* \* \* \* \*